United States Patent
Jacquemin

(10) Patent No.: US 7,765,861 B2
(45) Date of Patent: Aug. 3, 2010

(54) METHOD OF ADHESION MEASUREMENT AT THE INTERFACE BETWEEN LAYERS

(75) Inventor: Jean Philippe Jacquemin, Doubs (FR)

(73) Assignee: NXP B.V., Eindhoven (NL)

( * ) Notice: Subject to any disclaimer, the term of this patent is extended or adjusted under 35 U.S.C. 154(b) by 804 days.

(21) Appl. No.: 10/561,579

(22) PCT Filed: Oct. 31, 2003

(86) PCT No.: PCT/IB03/04883

§ 371 (c)(1),
(2), (4) Date: Jan. 17, 2008

(87) PCT Pub. No.: WO2004/042373

PCT Pub. Date: May 21, 2004

(65) Prior Publication Data

US 2009/0241656 A1    Oct. 1, 2009

(30) Foreign Application Priority Data

Nov. 6, 2002    (EP)    .................................. 02292769

(51) Int. Cl.
*G01N 19/04*    (2006.01)
(52) U.S. Cl. .................. 73/150 A; 73/788; 73/800; 73/801
(58) Field of Classification Search ........... 73/150 A, 73/788, 800, 801
See application file for complete search history.

(56) References Cited

U.S. PATENT DOCUMENTS

| | | | | |
|---|---|---|---|---|
| 3,605,486 A | * | 9/1971 | Anderholm et al. | 73/788 |
| 4,004,456 A | * | 1/1977 | Vahaviolos | 73/801 |
| 4,100,808 A | * | 7/1978 | Evans et al. | 73/588 |
| 4,401,477 A | * | 8/1983 | Clauer et al. | 148/525 |
| 4,870,865 A | * | 10/1989 | Hane et al. | 73/572 |
| 4,952,063 A | * | 8/1990 | Opsal et al. | 356/432 |
| 4,972,720 A | * | 11/1990 | Wu | 73/801 |
| 5,088,327 A | * | 2/1992 | Gammell | 73/588 |
| 5,438,402 A | * | 8/1995 | Gupta | 356/35.5 |
| 5,546,811 A | * | 8/1996 | Rogers et al. | 73/800 |
| 5,748,318 A | * | 5/1998 | Maris et al. | 356/630 |
| 5,838,446 A | * | 11/1998 | Meth et al. | 356/632 |
| 5,844,684 A | * | 12/1998 | Maris et al. | 356/432 |
| 5,959,735 A | * | 9/1999 | Maris et al. | 356/632 |
| 6,069,703 A | * | 5/2000 | Banet et al. | 356/432 |
| 6,072,568 A | * | 6/2000 | Paton et al. | 356/32 |

(Continued)

FOREIGN PATENT DOCUMENTS

FR    2 681 427    3/1993

OTHER PUBLICATIONS

A. W. Stephens and J. L. Vossen: "Abstract: Measurement of Interfacial Bond Strength by Laser Spallation"; Journal of Vacuum Science and Technology; vol. 13, No. 1; Feb. 1976; pp. 38-29.

(Continued)

*Primary Examiner*—David A. Rogers

(57) ABSTRACT

The strength of adhesion between two layers is evaluated by applying a series of laser shocks directly to the surface of one of the layers. Adhesion strength is determined based on the wavelength and energy of the laser pulse creating the shock which causes rupture of the interface between the two layers.

5 Claims, 1 Drawing Sheet

U.S. PATENT DOCUMENTS

| | | | |
|---|---|---|---|
| 6,136,386 A * | 10/2000 | Nakahigashi et al. | 427/536 |
| 6,795,198 B1 * | 9/2004 | Fuchs et al. | 356/521 |
| 6,848,321 B2 * | 2/2005 | Bossi et al. | 73/842 |
| 7,507,312 B2 * | 3/2009 | Bossi et al. | 156/344 |
| 7,509,876 B1 * | 3/2009 | Sokol et al. | 73/827 |
| 2005/0120803 A1 * | 6/2005 | Sokol et al. | 73/801 |
| 2008/0257048 A1 * | 10/2008 | Walters et al. | 73/588 |

OTHER PUBLICATIONS

J. H. Jeong et al: Intrinsic Stress in Chemical Vapour Deposited Diamond Films: An Analytical . . . ; Journal of Applied Physics 90(3); pp. 1227-1236; Aug. 1, 2001.

Michel Godin et al. :"Quantitative Surface Stress Managements Using a Microcantilever"; Applied Physics Letters 79(4); pp. 551-553; Jul. 23, 2001.

R.H. Dauskardt et al: "Adhesion and Debonding of Multi-Layer Thin Film Structures"; Engineering Fracture Mechanics 61(1998); pp. 141-162.

Guray Tas et al: "Electron Diffusion in Metals Studied by Picosecond Ultrasonics"; Physical Review; pp. 15 046-15 054; vol. 49 (21); Jun. 1, 1994.

* cited by examiner

METHOD OF ADHESION MEASUREMENT AT THE INTERFACE BETWEEN LAYERS

FIELD OF THE INVENTION

The present invention relates to a method of measurement of adhesion strength and, more particularly, to a method of measurement of adhesion strength at the interface between layers in a multi-layer stack, especially in a multi-material stack.

BACKGROUND ART

Microelectronic devices comprising integrated circuits may comprise stacks of layers. There are many situations in which it is desirable to measure the adhesion strength between two layers of material. Typically, this is a requirement during manufacturing processes of said microelectronic devices, when testing products for reliability. Often the two layers will consist of different materials, but it can also arise that there is an interface between two layers made of substantially the same material.

During manufacture of such microelectronic devices comprising integrated circuits, it is desirable to measure the adhesion strength between layers in a wafer, notably layers deposited as thin films. Ideally this would be done at various locations across the surface of the wafer. Wafer-testing techniques used to date involving stress-measurement techniques such as the curvature method, or x-ray measurement are described in the publication entitled "Intrinsic stress in chemical vapour deposited diamond films: An analytical model for the plastic deformation of the Si substrate" by J. H. Jeong et al, in the Journal of Applied Physics, 90(3), pp 1227-1236, 1 Aug. 2001. However, these techniques only provide information about residual stress in the wafer in general, they do not provide a measurement of adhesion strength between the different layers in the wafer at specific locations on the wafer.

In other fields, various measurement techniques are known which do allow adhesion-strength to be determined. Tests including stress measurement using a microcantilever are known from the publication entitled "Quantitative surface stress measurement using a microcantilever" by M. Godin et al, in Applied Physics Letters, 79(4), pp 551-553, 23 Jul. 2001. Methods that also include four-point bending techniques are already known from the publication entitled "Adhesion and de-bonding of multi-layer thin film structure" by Dauskardt et al in Eng. Fract. Mech, 61, pp 141-162, 1998.However, the above cited tests are destructive: they require the use of samples of a certain size and said samples are unsuitable for use after testing. Moreover, these known techniques are not well-suited to multi-material stacks involving thin films of the kind encountered in microelectronic devices.

Other adhesion-strength measurement techniques are known in which the interface between two materials is supplied with power from a laser.

For example, U.S. Pat. No. 4,972,720 describes a technique for assessing adhesion strength at an interface by heating the interface and evaluating the temperature at which thermal debonding occurs. The interface can be heated by applying laser energy over a relatively extended period (e.g. 5 seconds), and debonding can be detected by various techniques including using an acoustic sensor. The above cited patent U.S. Pat. No. 4,972,720 teaches that interfaces having lower adhesion strength produce noisier debonding events.

There are various disadvantages of the method described in U.S. Pat. No. 4,972,720. Firstly, the materials under test may experience an undesirable change in properties when they are heated. For example, a heated steel sample could undergo a martensitic transformation. Secondly, this known technique will only work when applied to the interface between two materials having different coefficients of thermal expansion.

U.S. Pat. No. 5,838,446 describes a technique for determining the strength of adhesion of a transparent coating provided on an opaque basecoat. Laser energy is used to ablate the basecoat at the interface between the basecoat and clearcoat such that a blister forms. Adhesion strength is determined from various parameters including the size of the blister, and a critical energy value at which a crack begins to propagate from the blister. A single IR ($\lambda$=1053 nm) laser pulse of 50 ps width is used to irradiate a single spot on the sample, then the energy value of the laser is changed and a new spot irradiated. At each spot, the radius of the blister that is formed is measured. The radius values from a series of spots are plotted on a graph in order to estimate a radius value for the critical energy. Calculation of the adhesion strength uses this estimated radius value.

There are disadvantages, too, with the method described in U.S. Pat. No. 5,838,446. Notably, ablation of materials is likely to generate dust, which will be undesirable in many manufacturing environments, e.g. in the microelectronics industry. Moreover, this technique requires use of a particular sample geometry which involves handling the sample to an extent which may be undesirable (e.g. if the sample is a semiconductor wafer being used to manufacture microelectronics devices). Further, in order to calculate a single adhesion strength value, measurements must be taken at a number of locations on the sample and the resultant data combined— leading to undue complication and a relatively lengthy calculation time.

U.S. Pat. No. 5,438,402 describes a laser spallation technique for determining tensile strength at the interface between a substrate and a coating. In such laser spallation techniques, a mechanical impulse is applied to the substrate and coating. In order for the mechanical impulse to be transmitted to the substrate/coating, it is necessary to provide an energy-absorbing coating on the free surface of the substrate (the surface remote from the coating), and a confinement plate on the energy-absorbing layer. A pulse from a laser is used as the energy source in this arrangement. Adhesion strength is calculated based on the movement of the free surface of the coating.

It is an object of the present invention to provide a new technique for evaluating adhesion strength at an interface between two layers, for example between layers of two different materials in a multi-material stack.

Preferred embodiments of the present invention provide an adhesion-strength evaluation method which is simpler to implement than the methods known heretofore. More particularly, in these preferred embodiments, a value for adhesion strength can be calculated without the need to process data relating to a set of locations on the sample or the need to use a complicated confinement structure.

Preferred embodiments of the invention allow adhesion strength to be measured at discrete locations over a surface.

The present invention provides a method of measuring adhesion strength at the interface between two layers, in which method a laser pulse is caused to impact directly on one of said two layers so as to produce a shock wave at the interface, and a sensor detects rupture of the interface (debonding). The adhesion strength at the interface between the two layers is determined based on the energy and wavelength of the laser pulse required to produce the rupture of the interface.

This technique is extremely simple to put into operation. Adhesion strength can be calculated based on parameters relating to a laser impact at a single point, thus simplifying and speeding up calculation. Moreover, this technique merely involves placing of a wafer, or other multi-material sample, on a pedestal; there is no need to arrange the sample relative to energy absorption layers or confinement plates.

The present invention allows adhesion strength to be measured in a manner which is not globally destructive of the tested sample and without generation of dust. Although there is disruption of the interface at the point(s) where testing is performed, the remainder of the sample is still useable. Thus, the present method is well-suited to testing adhesion strength between layers on a semiconductor wafer which is to be cut up into discrete devices.

Various types of sensor can be used to detect the rupture of the interface between the two layers undergoing test. In preferred embodiments of the invention the sensor is an acoustic sensor or an x-ray reflection device.

The invention and additional features, which may be optionally used to implement the invention to advantage, are apparent from and elucidated with reference to the drawing described hereinafter.

BRIEF DESCRIPTION OF THE DRAWINGS

FIG. 1 is a schematic representation of an arrangement of equipment used to implement a preferred embodiment of the method of the present invention, in which:

DETAILED DESCRIPTION OF THE EMBODIMENTS

Figure 1A:
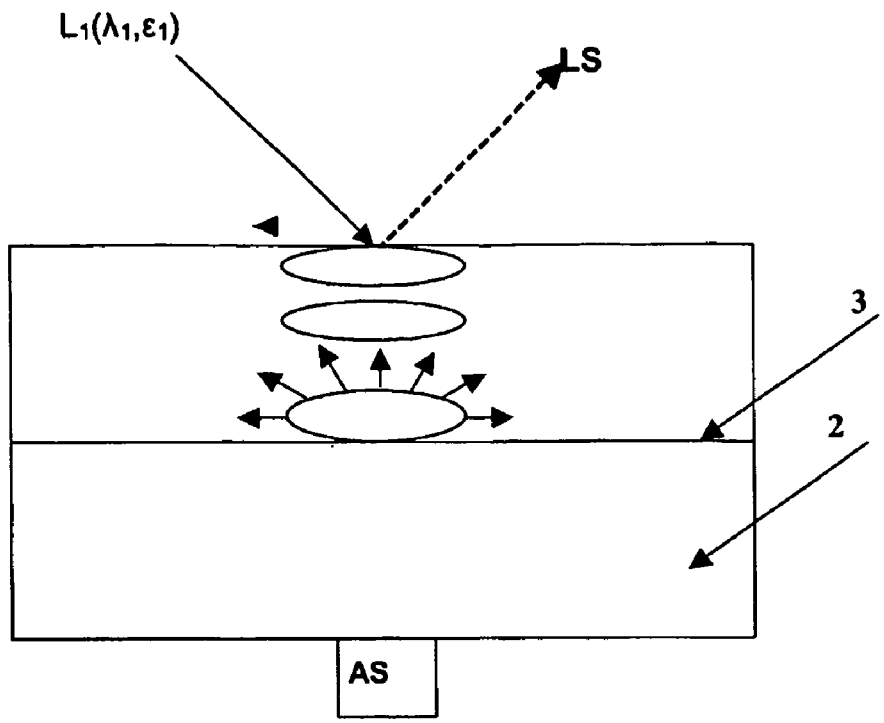
FIG. 1(a) illustrates the case where the interface between materials retains integrity.

The stress caused by a laser shock applied to a material depends upon the wavelength and the energy of the laser pulse used to produce the shock. More particularly, the higher the wavelength and energy of the laser pulse, the greater the stress that is caused. The behaviour of a surface undergoing a laser shock is described in more detail in "Electron diffusion in metals studied by picosecond ultrasonics" by G. Tas et al, appearing in Physical Review B, 46(21), pp 15046-15055, 1 Jun. 1994.

A laser pulse of appropriate wavelength and energy, impacting directly on a layer of material, can create sufficient stress at the interface between that layer and another to which it is bonded so as to overcome the forces of adhesion between those two layers. (This rupture of the interface between the two layers can be detected, for example using an acoustic sensor or x-ray reflection device. The adhesion strength between the two layers can thus be determined by applying laser pulses of increasing wavelength and/or energy directly to a sample undergoing test, noting the wavelength and energy of the laser pulse which just causes sufficient stresses to provoke rupture of the interface, and calculating a value for adhesion strength based on these critical values of wavelength and energy.

A laser shock can apply a pressure of up to 300 MPa or more which is generally adequate to crack the interface between two layers of material. For example, the adhesion strength of the interface between a layer of Ni and a layer of $Si_3N_4$ is approximately 100 MPa; the adhesion strength of the interface between a layer of Al and a layer of $Si_3N_4$ is approximately 100 MPa; and the adhesion strength of the interface between a layer of Nb and a layer of $Al_2O_3$ is approximately 300 MPa. Thus, the technique of the present invention can effectively be applied for measurement of adhesion strength.

A preferred embodiment of method of measuring adhesion strength between two layers, according to the present invention, will now be described with reference to FIG. 1. In this example, the adhesion strength is being measured at the interface between two layers in a stack which consists only of those two layers. However, the interface under test may be between the two outermost layers in a stack consisting of 3 or more layers, or the interface could correspond to the weakest interface within a stack of 3 or more materials, neither of the layers at the interface being at the surface of the stack.

Typically, this technique will be applied for measurement of adhesion strength between two layers 1, 2 in a semiconductor wafer product. Typically, when adhesion strength in a semiconductor wafer is being measured, layer 1 could correspond to a copper layer deposited on a barrier layer 2 made of TaN. However, there are numerous other possibilities: for example, the present method could be used to measure adhesion strength at the interface between a TaN barrier layer and an underlying $SiO_2$ layer, between TaN and FSG, between Cu on SiN, etc.

Figure 1B:
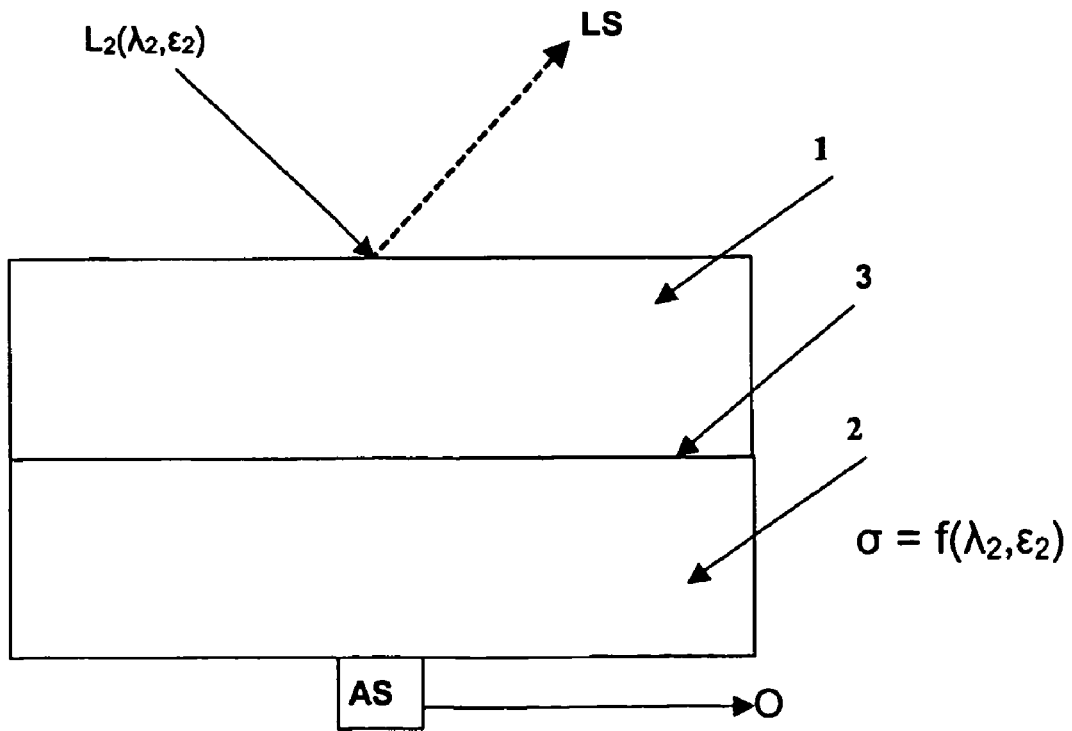
FIG. 1(b) illustrates the case where the interface cracks.

As illustrated in FIG. 1(a), according to the present invention, a laser pulse $L_1$ at a first wavelength $\lambda_1$ and having a first energy $\epsilon_1$ is directed at a sample under test so as directly to impact the free surface of one of the two layers between which adhesion strength is to be measured. The pulse duration is typically several tens to hundreds of nanoseconds, and will depend upon the hardware used to produce the laser pulse. As examples, an Nd-YAG laser or an Excimer laser could be used. However, it is preferred to use a colouring laser which can output different wavelengths. In the illustrated example the laser pulse $L_1$ is caused to impact layer 1 directly. The laser impact causes a shock wave to propagate through the first layer 1 towards the interface 3 with the second layer 2. The progression of the shock wave is illustrate by a series of white ovals in FIG. 1(a). When the shock wave reaches the interface 3 it causes stress as indicated by the arrows in the figure.

In the case illustrated in FIG. 1(a), the wavelength and energy of the laser pulse are insufficient to cause debonding of the first and second layers 1, 2. Accordingly, no sound is detected by an acoustic sensor AS which is arranged in contact with the second layer 2.

The wavelength and/or energy of the laser pulse is increased and a second pulse is applied to the free surface of the layer 1 at the same location. Eventually, values of wavelength ($\lambda_2$) and energy ($\epsilon_2$) are reached at which the laser pulse $L_2$ causes stresses which are sufficient to cause the first and second layers 1, 2 to separate, in other words the interface 3 cracks. This event creates a sound, the sound waves propagate through the second layer 2 (as illustrated by the black ovals in FIG. 1(b)) and can be detected, for example, using the acoustic sensor AS, which outputs a signal O. The adhesion strength ($\sigma_{1,2}$) between the layers 1, 2 is a function of these values of wavelength and energy ($\lambda_2$, $\epsilon_2$). More particularly, the pressure, P, at the surface of the sample can be determined from the following equation:

$$P=0.622 A^{7/16} Z^{-9/16} \lambda^{-1/4} \tau^{-1/8} I^{3/4},$$

where A is the atomic weight of the layer 1, Z is the ionisation degree of the plasma, $\lambda$ is the wavelength of the laser, $\tau$ is the pulse duration and I is the maximum power density of the plasma. (Incidentally, in the case where the laser shock wave traverses more than one layer before reaching the interface undergoing test, the above equation is applied to each layer traversed).

In a case where a colouring laser is used, it is preferred to set the wavelength of the laser pulse to a first value, $\lambda_i$, and the pulse energy to a first value $\epsilon_i$, before applying the first pulse to the sample at a given location. If the resulting laser shock is insufficient to cause debonding at the interface 3, then the pulse energy is increased by an increment $\Delta\epsilon$, and a second pulse is applied to the sample at the same point. The method continues, increasing the laser pulse energy in steps until either debonding occurs at the interface 3 or the maximum possible pulse energy for the laser is reached. If the maximum pulse energy is reached before debonding occurs, then the wavelength of the laser is increased by an increment , the pulse energy returned to its lowest value, and the process repeated at the new wavelength. Eventually, the wavelength ($\lambda_2$) and energy ($\epsilon_2$) values necessary to produce debonding will be reached.

In a case where a single-wavelength laser is used, the testing process preferably consists in setting the pulse energy at an initial value $\epsilon'_i$ for the first pulse applied to the sample, then ramping up the energy value by an increment $\Delta\epsilon'$ for each subsequent laser pulse, until debonding is detected. Preferably, a laser sensor LS (e.g. a photo-diode) is provided to detect laser light exiting from the free surface of layer 1, namely the light reflected from the free surface of the layer 1 and from the interface between the layers 1/2. The thickness of the first layer can be determined based on the signal detected by the laser sensor LS. Preferably the metapulse technique is used for this purpose.

Further details of the construction of the laser source, acoustic sensor and laser sensor are not given here because conventional devices can be used to implement these components used in the preferred embodiment of the invention. However, it should be mentioned that the acoustic sensor can be an active or a passive type.

As mentioned above, the adhesion-strength measuring technique of the invention can be used to measure adhesion strength between layers, at different points on a surface. In other words, a series of laser pulses of increasing energy/wavelength would be applied at a point A, until debonding occurs between the layers 1, 2 at point A, then the point of impact on the surface 1 would be changed to a new location, point B. In the above-described embodiment, these points can be spaced apart from each other by a distance of approximately 1 centimeter, or greater.

The drawings and their description hereinbefore illustrate rather than limit the invention. It will be evident that there are numerous alternatives that fall within the scope of the appended claims. For example, although the above-described preferred embodiment illustrated measurement of adhesion strength in a sample comprising two layers, the method according to the invention can also be applied for measurement of adhesion strength between two layers of a sample comprising three or more layers. In such a case, the laser shock will cause debonding at the weakest interface.

Furthermore, in the above description of a preferred embodiment of the present invention, it was stated that the energy of successive laser pulses applied at a test point using a colouring laser would be stepped up by an increment of constant size, from an initial lowest value up to a maximum value for the laser being used, before increasing the wavelength from a low value to the next highest value. However, other patterns of variation of the pulse energy/wavelength are possible. For example, depending upon the nature of the sample under test, it may be preferred to start with a pulse energy which is already close to the maximum and/or with a wavelength which is not the lowest wavelength of the laser. Moreover, the size of the increment in energy and/or wavelength may be set differently depending upon the nature of the material(s) at the interface undergoing test.

Any reference sign in a claim should not be construed as limiting the claim.

The invention claimed is:

1. A method of measuring adhesion strength between first and second layers of material in a stack of two or more layers, the first and second layers being in contact at an interface, the method comprising steps of:
    applying a plurality of laser shocks directly to a free surface of said stack of layers by causing a plurality of laser pulses of respective different wavelength and/or energy to impact said free surface,
    detecting cracking of the interface on application of one of said plurality of laser pulses;
    determining the wavelength and energy of the applied laser pulse causing cracking of the interface; and
    calculating a value for adhesion strength of the first and second layers based upon the determined wavelength and energy values.

2. The adhesion-strength measurement method of claim 1, wherein the laser shock application step comprises applying said plurality of laser pulses at the same location on the free surface of said stack until cracking of the interface is detected.

3. The adhesion-strength measurement method of claim 1, wherein the detecting step comprises detecting cracking using an acoustic sensor.

4. The adhesion-strength measurement method of claim 1, wherein said first and second layers are layers of a semiconductor wafer product.

5. The adhesion-strength measurement method of claim 1, wherein said first layer is at one end of the said stack and a surface of said first layer constitutes the free surface of the stack on which the laser pulses impact.

* * * * *